United States Patent [19]
Cumming et al.

[11] Patent Number: 5,804,971
[45] Date of Patent: Sep. 8, 1998

[54] MODULAR CARD BASED METER

[75] Inventors: Colin J. Cumming, Stillwater; Philip M. Maltby, Tulsa, both of Okla.

[73] Assignee: Nomadics, Inc., Stillwater, Okla.

[21] Appl. No.: 609,176

[22] Filed: Mar. 1, 1996

[51] Int. Cl.$^6$ .................................................. G01N 27/416
[52] U.S. Cl. .......................... 324/438; 324/439; 204/406; 204/433; 422/82.03
[58] Field of Search ..................... 324/425, 438, 324/439, 71.1; 204/406, 408, 416, 433; 422/82.03

[56] References Cited

U.S. PATENT DOCUMENTS

| | | | |
|---|---|---|---|
| 4,260,950 | 4/1981 | Hadden et al. | 324/438 |
| 4,752,740 | 6/1988 | Steininger | 324/438 |
| 5,016,201 | 5/1991 | Bryan et al. | 204/412 X |
| 5,096,669 | 3/1992 | Lauks et al. | 324/438 X |
| 5,103,179 | 4/1992 | Thomas et al. | 324/438 |
| 5,108,578 | 4/1992 | Somes et al. | 204/433 |
| 5,126,937 | 6/1992 | Yamaguchi et al. | 422/82.03 X |
| 5,198,093 | 3/1993 | Sydlowski et al. | 204/406 |
| 5,248,403 | 9/1993 | Tomita et al. | 204/433 X |
| 5,422,825 | 6/1995 | Lin et al. | 204/406 X |
| 5,690,893 | 11/1997 | Ozawa et al. | 422/82.03 |

*Primary Examiner*—Glenn W. Brown
*Attorney, Agent, or Firm*—Dougherty & Hessin, P.C.

[57] ABSTRACT

The invention relates to a sensor electrode connected to a card module that can be received within an industry standard plug-in receptacle of a selected computer to enable a combination capable of very exhaustive data detection, processing, storage and the like for whatever the selected data sensor and particular card module.

39 Claims, 2 Drawing Sheets

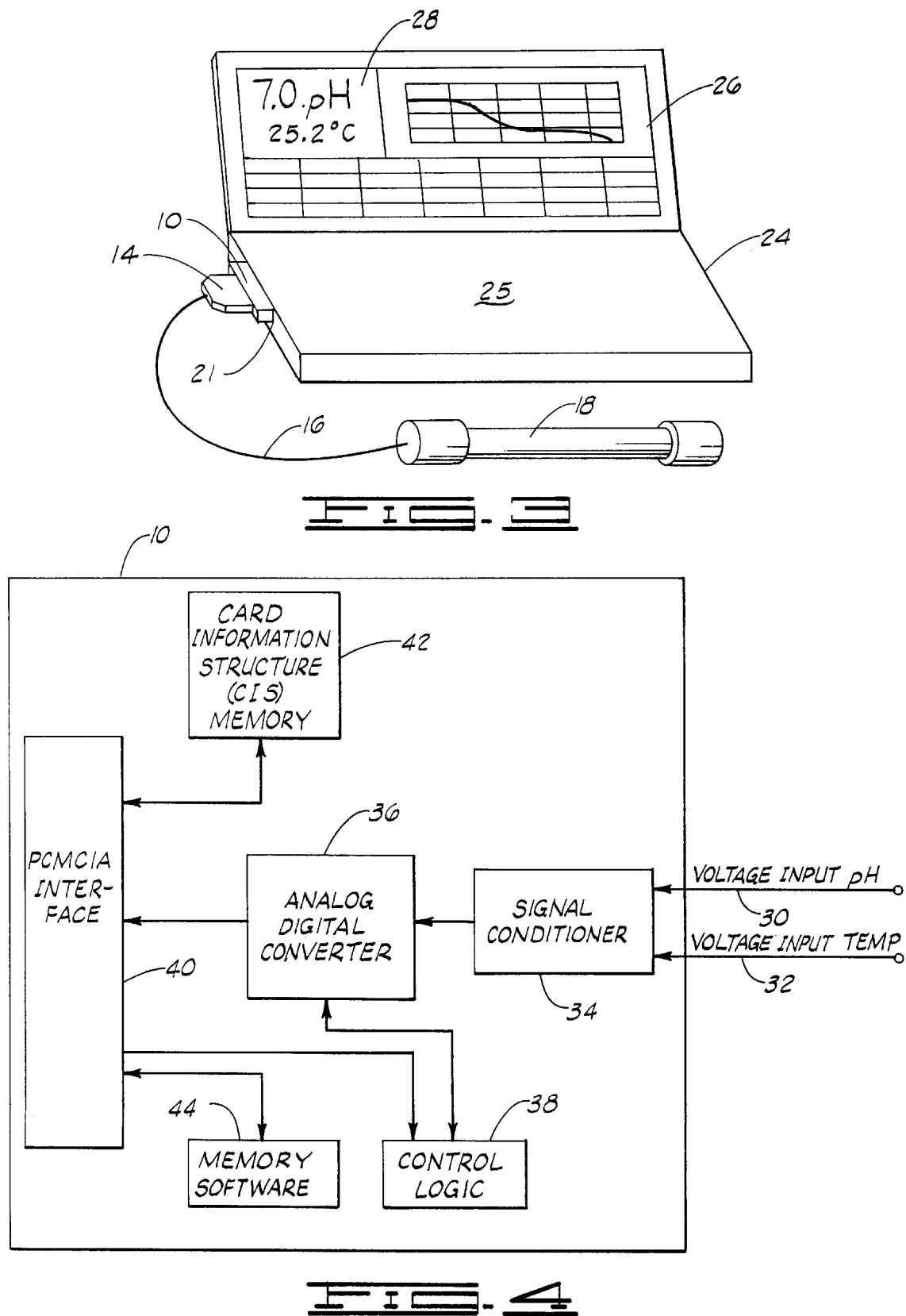

MODULAR CARD BASED METER

BACKGROUND OF THE INVENTION

1. Field of the Invention

The invention relates generally to the field of instrumentation for electrochemical measurement and, more particularly, but not by way of limitation, it relates to an improved modular meter assembly for determining and logging pH and other concentration values.

2. Description of the Prior Art

There are a variety of portable analytical instruments that may be used for measuring ion concentration. These instruments generally consist of a base unit and an electrode assembly that are connected by cable, and such a portable metering unit generally contains circuitry for measuring, processing and display of the resultant values. See U.S. Pat. No. 4,260,950. In addition to the portable instruments, there are a wide variety of benchtop instruments which perform similar functions but are generally not intended to be moved during operation. Some of these instruments contain the means to store certain values and such storage capacity is usually limited to a few dozen readings. These instruments also may provide the means to perform calibration so that the readings made with a specific attached electrode are accurate and, in some cases, there is included a capability to store the calibration information in the device.

Since it is often necessary or desirable to process or archive the measured values using a computer of some type, several meters provide the means to transfer the measured values to a computer via a standard RS-232C connector. See U.S. Pats. Nos. 5,108,578 and 5,198,093. The difficulty of such transfer to computer for subsequent processing, storage, display, archiving and further communication is a serious limitation of current instrumentation. Existing instruments provide results to the user via a dedicated alphanumeric display, and these displays are limited in the amount of information that they can convey. Such limitation issues from the fact that the displays are fixed function LED or LCD devices. In order to display several values or other information such as instrument diagnostics or instructions, it is necessary to multiplex the use of the display, tending to make operation complex and to cause user difficulty and operational errors.

SUMMARY OF THE INVENTION

The present invention relates to an electrochemical metering device that consists of a plug-in module that can be inserted into standard PCMCIA slot-equipped computers. The plug-in module provides for the connection of a standard electrochemical sensing electrode and, if desired, a temperature sensor, all of which comply with a standard established for computers for interfacing the module with the plug-in slot. The invention further includes computer software that operates in the associated computer in concert with the plug-in module. The module under control of the software performs the measurement and the raw values are passed to the software which is executing on the host computer. This software can perform processing such as calibration and units conversion to provide results to the user via the computer screen and, because the computer has a vast amount of processing power at its disposal, it can perform sophisticated processing of the data with subsequent storage in large quantities.

Therefore, it is an object of the present invention to provide an electrochemical metering apparatus that is accurate and convenient in use.

It is also an object of the invention to make electrochemical measurements and perform computations, processing, display, storage and the communication of measured information directly with an associated host computer.

It is yet further an object of the present invention to sense and measure data for subsequent presentation in useful graphic presentations.

It is still another object of the invention to connect interactively a standard form of sensor through a module to a selected host computer to enable accurate sensed data for subsequent processing.

Finally, it is an object of the invention to provide a device wherein the measured data can also be processed and displayed on the generally substantial display resources of the associated computer.

Other objects and advantages of the invention will be evident from the following detailed description when read in conjunction with the accompanying drawings that illustrate the invention.

BRIEF DESCRIPTION OF THE DRAWINGS

FIG. 3 is an isometric view of the card module inserted into the PCMCIA slot of a laptop computer showing a typical screen that displays measurement data; and FIG. 4 is a block diagram representation of the various components of the card module.

DETAILED DESCRIPTION OF THE INVENTION

Figure 1:
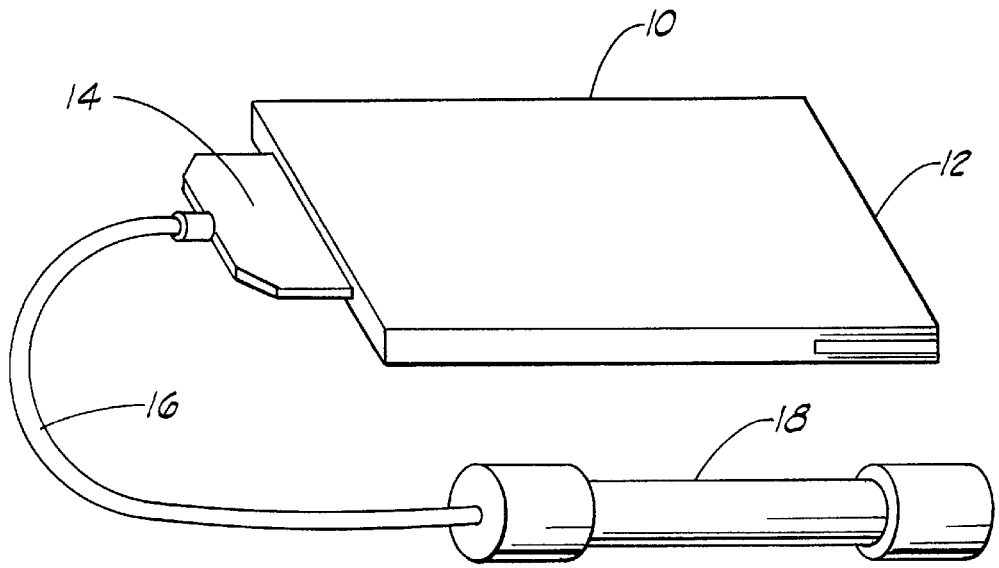
FIG. 1 is an isometric view of a card module and attached electrode.
Figure 2:
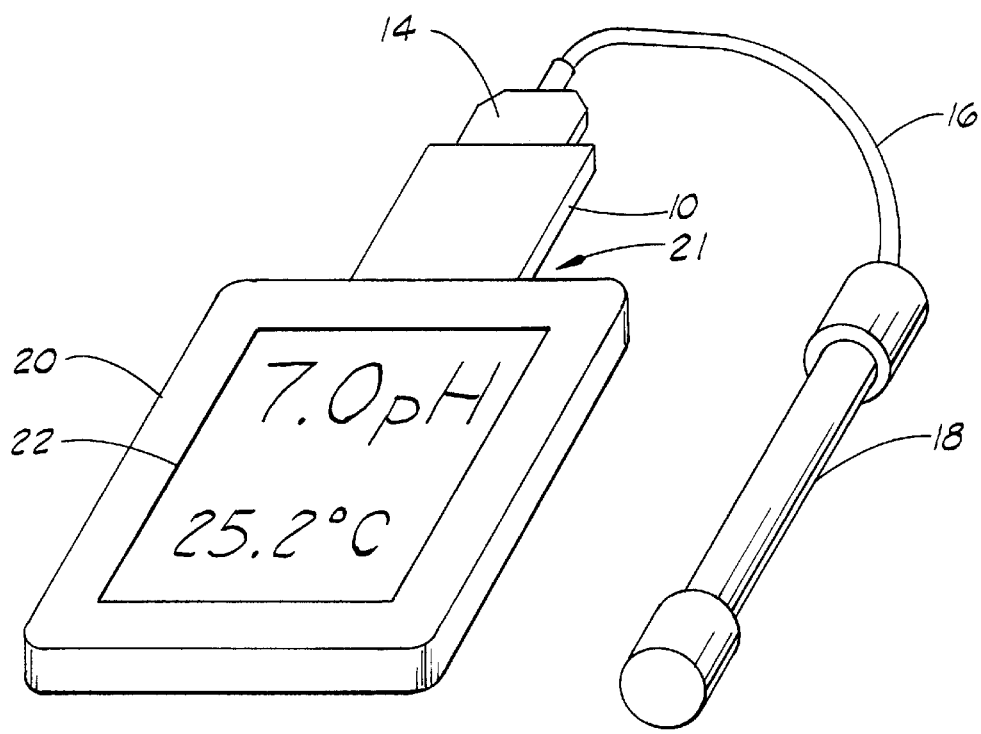
FIG. 2 is an isometric view of the card module showing partial insertion into the PCMCIA slot of a personal digital assistant (PDA) or similar hand-held type device.

FIGS. 1–3 illustrate the card module 10 and its relationship to a selected host computer. In FIG. 1, the card module 10 is a Type II PCMCIA card which is a module interface defined by The Personal Computer Memory Card International Association to provide a common means for interfacing memory and peripherals to computers by means of a convenient plug-in slot. The standard card module 10 includes a large plurality of plug-in connector pins (e.g., 68) on the insertion end 12 as well as a number of connections to connector 14.

The plug 14 is then connected to a cable 16 leading to a selected type of electrode 18. The electrode 18 is preferably a three-in-one type that incorporates a reference electrode, a sense electrode, and a temperature sensor all within a single electrode body. This is a standard electrode configuration; however, separate electrodes and/or temperature sensors could be used simply by employing a different cabling scheme.

FIG. 2 shows the electrode 18 and card module 10 when partially inserted into a personal digital assistant (PDA) 20 at the associated PCMCIA slot 21. The PDA class of devices is a lesser capacity computer, e.g., a hand-held computer such as the Apple "Newton". The PDA 20 includes a display screen 22 to provide read-out of the metered quantities, in this case ion concentration (7.0) and temperature (25.2° C.). The control software is resident in the PDA 20 in most cases but, in some cases, it may be in the card module 10, as will be described. In FIG. 2, the combination of card module 10, PDA 20 (computing device) with software, and electrode 18 produce a complete measurement capability.

Referring now to FIG. 3, the metering device consists of a typical laptop or palmtop type host computer 24 with the PCMCIA slot 21 receiving the card module 10 that is coupled to the electrode 18 by means of plug 14 and cable 16. A keyboard (not shown) is disposed in the lower panel 25. A display screen 26 on computer 24 shows a typical display 28 which includes ion concentration and temperature readings. In addition, a graphic chart may be included whereon results can be plotted over a predetermined duration. Also, a table or spreadsheet may be displayed as another means for recording a variety of data versus time. Preferably the laptop host computer 24 will have greater capability such that a number of other data quantities and evaluations will require display. Nearly equivalent capability may be achieved using an HP 100LX palmtop as the host computer.

Referring now to FIG. 4, the microcircuitry within the card module 10 includes among input/output connections, the voltage input 30 for ion concentration data and input 32 for temperature. The inputs are applied to a signal conditioner 34, a high impedance input buffer, which is necessary for interfacing with typical ion concentration probes. Once conditioned, the input signals are input to an analog-to-digital converter 36 that provides output of counterpart digital signals for input to control logic 38 and the PCMCIA interface 40. The card module 10 is controlled by commands sent over PCMCIA interface 40 and received and interpreted by control logic 38 on card module 10. Control logic 38 performs all address decoding and operation sequencing on card module 10. The conversion process and the timing and sequencing of events are performed under software control in the host computer.

The software executes within the host computer processor as it communicates with the card module 10 via the standard PCMCIA interface 40. The card module 10 includes a memory 42, known as the Card Information Structure (CIS), and the software reads this memory 42 to establish the identification of the card module 10. Card module 10 also includes memory 44 which may also be used to store the software program, measured data values, calibration values or some combination of this information.

In order to use the invention with standard laptop type computers, the software can be provided on a floppy disk; however, some PDA's and other small computers do not have provisions for a floppy. In order to use the smaller computers as host, the memory 44 on card module 10 is provided for storing the operating software. Once the software is so stored, the card module 10 becomes a self-contained instrument. The memory 44 can also be used to store measurements thus allowing the data to be removed from the host computer by means of the card module 10. Calibration values can also be stored in memory 44 of card module 10, thus ensuring that calibration values are always available, even when card module 10 is moved from one host computer to another.

The present invention provides hardware and software that will convert portable computers such as laptops, palmtops and personal digital assistants into powerful, low cost portable instrumentation. The basic elements of the technology are sophisticated software and miniaturized electronics contained within the PCMCIA card modules, industry standard plug-in devices. A listout of the program object code for host computer control is included herewith as "Exhibit—HOST PROGRAM"(see microfiche appendix).

A field technician may carry a pocket-sized host computer and a wallet full of card modules 10, each providing a different sensor measurement function when used in concert with the host computer. Instrument capabilities currently available in card module format are as follows:

pH/ORP/ISE measurement system
dual probe pH measurement system
multi-input pH measurement system
conductivity measurement system
ion specific measurement system
titration system
dissolved oxygen system
water analysis system
humidity/temperature measurement system.

The foregoing discloses a novel form of instrumentation wherein the PCMCIA card module serves as the unifying element between a selected electrochemical sensor and a host computer. In many cases, the PCMCIA based sensor can be used with the portable computer that is already carried by the field technician. This allows the processing and data reduction and storage capabilities of the computer to be used for processing and storing the sensor data. As new and more powerful computers become available, the instrument can be upgraded and software commonality can be retained thereby to protect the software investment.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. An ion concentration metering device, comprising:

an electrochemical sensing electrode providing an output voltage indicative of pH data;

a standard card module;

means for conducting said output voltage to said standard card module;

a host computer receiving said card module in a PCMCIA standard plug interface; and software executing within said host computer to process and display pH data responsive to said output voltage.

2. An ion concentration metering device as set forth in claim 1 which further includes:

a temperature sensing electrode providing an output voltage indicative of temperature data for conduction to said standard card module.

3. An ion concentration metering device as set forth in claim 1 wherein said standard card module includes:

input buffer means receiving said output voltage and providing a conditioned signal output;

an analog to digital converter receiving said conditioned signal output and generating counterpart digital signals;

control logic interactive with said digital signals; and a PCMCIA interface for connection to said PCMCIA standard plug interface.

4. A metering device, comprising:

a host computer having a PCMCIA slot communicating to the exterior;

a software program operable in the host computer for calibrating and controlling a metering operation;

a selected electrode for metering an electrochemical value; and a card module connected to said electrode, said card module being plugged into said host computer PCMCIA slot.

5. A metering device as set forth in claim 4 wherein: said host computer is a personal digital assistant.

6. A metering device as set forth in claim 4 wherein:
said host computer is a laptop computer.

7. A metering device as set forth in claim 4 wherein:
said host computer is a palmtop computer.

8. A metering device as set forth in claim 4 wherein:
said selected electrode meters pH and temperature.

9. A measurement system, comprising:
a sensor providing an output signal indicative of a measurement value;
a card module connected to said sensor;
a host computer receiving said card module in a PCMCIA standard plug interface; and
software executing within said host computer to process and display said measurement value.

10. A measurement system as set forth in claim 9 wherein:
said software is contained on said card module so that the card module is operative to effect the entire measurement.

11. A measurement system as set forth in claim 10 wherein:
the card module contains calibration values such that said card module becomes moveable between host computers while remaining in calibration.

12. A measurement system as set forth in claim 9 wherein:
the card module contains calibration values such that said card module becomes moveable between host computers while remaining in calibration.

13. A measurement system as set forth in claim 9 wherein:
the measurement value is stored on the card module.

14. A measurement system, comprising:
a sensing device;
a plug-in card module connected to said sensing device; and
a hand-portable host computer having a plug-in slot receiving said plug-in card module, wherein said sensing device, said plug-in card module and said host computer together provide a complete hand-portable measurement capability.

15. A measurement system as set forth in claim 14 wherein said plug-in card module includes a memory having software stored therein for execution by said host computer in providing the measurement capability.

16. A measurement system as set forth in claim 15 wherein said memory includes storage space for storing measurement data generated by said host computer in response to said host computer executing said software.

17. A measurement system as set forth in claim 14 wherein said plug-in card module includes a memory having storage space to store measurement data generated by said host computer in response to sensing by said sensing device such that said measurement data is transportable with said plug-in card module when said card module is removed from said plug-in slot.

18. A measurement system as set forth in claim 17 wherein said memory has control software stored therein for execution by said host computer to generate said measurement data for storage in said memory.

19. A measurement system as set forth in claim 18 wherein said memory further has calibration values stored therein.

20. A measurement system as set forth in claim 14 wherein said host computer is a personal digital assistant.

21. A measurement system as set forth in claim 14 wherein said host computer is a laptop computer.

22. A measurement system as set forth in claim 14 wherein said host computer is a palmtop computer.

23. Apparatus for a measurement system, comprising:
a plug-in card in compliance with an industry standard established for computers interfacing via a plug-in slot; and
means, mounted on said plug-in card, for enabling a host computer to operate as a measurement instrument in response to the host computer receiving said plug-in card in an industry standard plug-in slot of the host computer.

24. Apparatus as set forth in claim 23 wherein said means for enabling includes a memory having software stored therein for execution by the host computer in operating as the measurement instrument.

25. Apparatus as set forth in claim 24 wherein said memory includes storage space for storing measurement data generated by the host computer in response to the host computer executing said software.

26. Apparatus as set forth in claim 23 wherein said means for enabling includes a memory having storage space to store measurement data generated by the host computer such that said measurement data is transportable with said plug-in card when said card is removed from the plug-in slot of the host computer.

27. Apparatus as set forth in claim 26 wherein said memory has control software stored therein for execution by the host computer to generate said measurement data for storage in said memory.

28. Apparatus as set forth in claim 27 wherein said memory further has calibration values stored therein.

29. Apparatus as set forth in claim 23 wherein said means for enabling includes:
an input buffer to receive an output signal from a sensing device;
an analog to digital converter connected to said input buffer and connected to a portion of said card compliant with the industry standard established for computers interfacing via a plug-in slot;
control logic connected to said analog to digital converter and to another portion of said card compliant with the industry standard established for computers interfacing via a plug-in slot; and
a memory connected to a further portion of said card compliant with the industry standard established for computers interfacing via a plug-in slot.

30. Apparatus as set forth in claim 29 wherein said means for enabling further includes software stored in said memory for execution by the host computer in operating as the measurement instrument.

31. Apparatus as set forth in claim 30 wherein said memory includes storage space to store measurement data generated by the host computer in response to the host computer executing said software.

32. Apparatus as set forth in claim 23 further comprising a sensing device having a plug adapted to plug into said plug-in card.

33. Apparatus for a measurement system, comprising a plurality of plug-in card modules wherein each of said card modules is adapted to plug into an industry standard plug-in slot of a host computer and provides a different measurement function to the host computer when the respective card module is plugged into the plug-in slot of the host computer and the host computer is operated in response to software associated with the respective card module.

34. Apparatus as set forth in claim 33 further comprising a sensing device having a plug adapted to plug into said card modules.

35. Apparatus as set forth in claim 33 wherein each of said card modules includes a respective memory having the software associated therewith stored in said memory.

36. A method of measuring, comprising:

inserting a card module into an industry standard slot of a host computer;

providing an output signal from a sensing device connected to the card module;

processing the output signal on the card module and providing a processed signal to the host computer; and generating a measurement data signal in the host computer and providing a display from the host computer in response to the measurement data signal.

37. A method as set forth in claim 36 further comprising storing information in a memory of the card module in response to the measurement data signal and removing the card module from the host computer so that the stored information responsive to the measurement data signal is transportable with the card module separately from the host computer.

38. A method as set forth in claim 36 wherein generating a measurement data signal in the host computer includes executing in the host computer a software program stored in a memory of the card module.

39. A method as set forth in claim 36 wherein inserting a card module includes selecting the card module from a plurality of card modules, wherein each of the card modules provides a different measurement function to the host computer.

* * * * *